United States Patent
Sichel et al.

(10) Patent No.: US 9,207,225 B2
(45) Date of Patent: Dec. 8, 2015

(54) METHOD FOR DETECTING A CONCENTRATION OF CHLORATE-IONS IN AN AQUEOUS SOLUTION, APPARATUS FOR DETECTING A CONCENTRATION OF CHLORATE-IONS AND CONTROL UNIT

(75) Inventors: Cosima Sichel, Karlsruhe (DE); Johannes Stein, Ulm (DE)

(73) Assignee: Evoqua Water Technologies GmbH, Günzburg (DE)

( * ) Notice: Subject to any disclaimer, the term of this patent is extended or adjusted under 35 U.S.C. 154(b) by 322 days.

(21) Appl. No.: 13/584,395

(22) Filed: Aug. 13, 2012

(65) Prior Publication Data
US 2013/0037422 A1    Feb. 14, 2013

(30) Foreign Application Priority Data
Aug. 12, 2011    (EP) .................................. 11177346

(51) Int. Cl.
| | | |
|---|---|---|
| *G01N 33/18* | (2006.01) | |
| *G01N 33/00* | (2006.01) | |
| *G01N 21/59* | (2006.01) | |
| *G01N 21/63* | (2006.01) | |

(52) U.S. Cl.
CPC .......... *G01N 33/182* (2013.01); *G01N 21/5907* (2013.01); *G01N 21/631* (2013.01); *G01N 33/18* (2013.01); *Y10T 436/19* (2015.01); *Y10T 436/193333* (2015.01)

(58) Field of Classification Search
CPC ............ G01N 33/182; G01N 21/5907; G01N 21/631; G01N 33/18; G01N 33/00; G01N 21/59; G01N 21/17; G01N 21/62; Y10T 436/00; Y10T 436/11; Y10T 436/19; Y10T 436/193333; Y10Y 436/00; Y10Y 436/11; Y10Y 436/19; Y10Y 436/193333

USPC ........ 436/125; 205/778.5, 775; 204/406, 407, 204/400

See application file for complete search history.

(56) References Cited

U.S. PATENT DOCUMENTS

2011/0198239 A1*   8/2011   Foster ...................... 205/778.5

OTHER PUBLICATIONS

Kang, Namgoo et al., Photochemical Formatino of Perchlorate from Aqueous Oxychlorine Anions, Analytica Chimica Acta, vol. 567, No. 1, Elsevier, 2006, 9 pages.*
Dattilio Teri, et al, Method 327.0 Determination of Chlorine Dioxide and Chlorite Ion in Drinking Water Using Lissamine Green B and Horseradish Peroxidase With Detection by Visible Spectrophotometry, EPA, May 2005, pp. 327.0-1 to 327.0-30.*
Trautwein, Norman L. et al., "Spectrophotometric Determination of Chlorate Ion," Analytica Chimica Acta, Elsevier, vol. 41, 8 pages, Sep. 8, 1967.
Tang, Tsung-Fei et al., "Quantitative Determination of Chloride, Chlorite, and Chlorate Ions in a Mixture by Successive Potentiometric Titrations," Analytical Chemistry, American Chemical Society, vol. 52, No. 9, 4 pages, Aug. 1980.
(Continued)

*Primary Examiner* — Christine T Mui

(57) ABSTRACT

An apparatus, a control unit and a method are provided for detecting a concentration of chlorate-ions in an aqueous solution containing different types of chlorine oxidants. By applying energy to a defined volume of the aqueous solution to trigger a transformation of substantially all chlorine oxidants and/or chlorine therein to chloride and/or chlorate, and detecting the concentration of chlorate-ions contained in the defined volume, a solution can be provided that enables a simple and cheap measurement for a concentration of chlorate ions in an aqueous solution and that is capable for online measurement of such chlorate concentrations.

20 Claims, 3 Drawing Sheets

(56) References Cited

OTHER PUBLICATIONS

Siddiqui, Mohamed S. "Chlorine-Ozone Interactions: Formation of Chlorate," Water Research, vol. 30, No. 9, Elsevier Science Ltd., 11 pages, Feb. 1996.

Li, Xin-Ai et al., "Determination of Chloride, Chlorate and Perchlorate by PDMS Microchip Electrophoresis with Indirect Amperometric Detection," Talanta, vol. 75, No. 1, Elsevier, 6 pages, Oct. 26, 2007.

Hosseini, S. G. et al., "Spectrophotometric Determination of Chlorate Ions in Drinking Water," Science Direct, Desalination 245, 8 pages, Jun. 23, 2008.

European Search Report, Application No. 11177346.1, 8 pages, Jan. 25, 2012.

Australian Office Action, Application No. 2012211358, 3 pages, Aug. 26, 2013.

\* cited by examiner

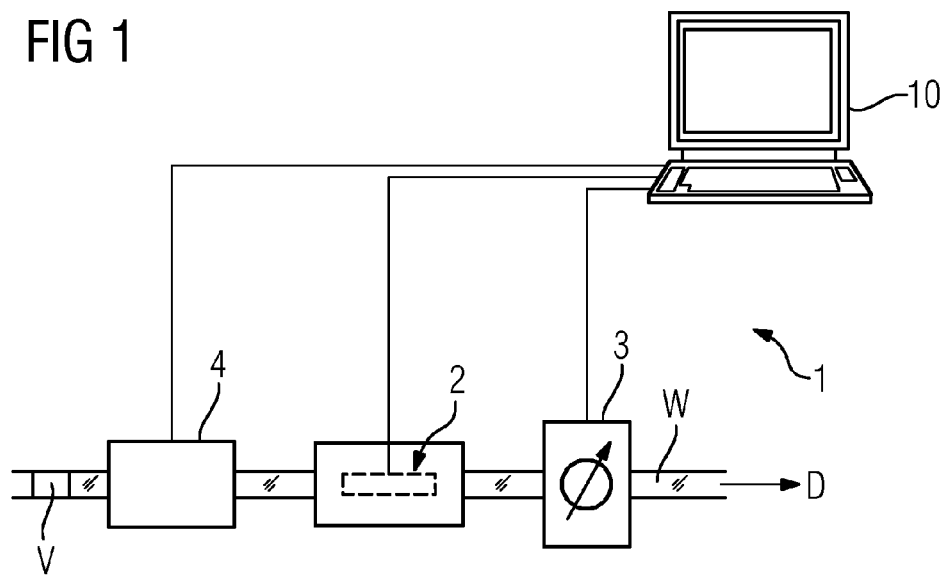
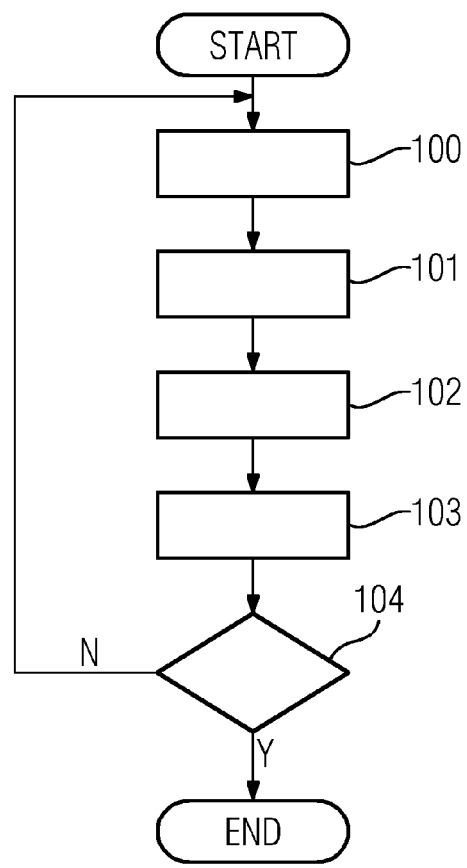

METHOD FOR DETECTING A CONCENTRATION OF CHLORATE-IONS IN AN AQUEOUS SOLUTION, APPARATUS FOR DETECTING A CONCENTRATION OF CHLORATE-IONS AND CONTROL UNIT

CROSS-REFERENCE TO RELATED APPLICATIONS

This application claims priority to EP Patent Application No. 11177346 filed Aug. 12, 2011. The contents of which is incorporated herein by reference in its entirety.

TECHNICAL FIELD

This disclosure concerns a method for detecting a concentration of chlorate-ions in an aqueous solution containing different types of chlorine oxidants. Additionally, the disclosure concerns an apparatus for detecting a concentration of chlorate-ions. Furthermore the disclosure concerns a control unit for an apparatus referenced above.

BACKGROUND

This disclosure deals with the field of water treatment, especially the technical field of water disinfection utilizing a chlorine species. Chlorine species are globally the most commonly used disinfectants for water.

An important drawback for chlorine based disinfection however is the production of so called "disinfection by-products" (DBPs). These by-products may have negative effect to health of organisms consuming such disinfected water containing these by-products.

Chlorine DBPs can be divided into organic and inorganic DBPs. For both groups strict limits have been set for disinfected waters by the respective institutions. For inorganic DBPs the most important species are chlorite ($ClO_2^-$) and chlorate $ClO_3^-$.

Chlorite has been already restricted in many countries due to its negative health effects, especially for humans. For chlorate less knowledge exists on the impact on human health but more and more studies give reason for further limitations for concentrations of chlorate in disinfected water, especially drinking water.

The introduction of threshold values for concentrations of chlorate in water sources is therefore expected in nearer future, e.g. for swimming pools. For other water sources, especially drinking water, similar steps are expected in the future. Already today the World Health Organization (WHO) recommends an upper threshold value for chlorate concentration of 1 milligram per liter for drinking water.

To restrict the concentration of chlorate in aqueous solutions to certain maximum level, it is necessary to be able to measure the concentrations of chlorate-ions in aqueous solutions.

Today such measurements can be provided by ion chromatography. These methods are able to do an offline analysis with specific samples of the aqueous solution. These kinds of measurements generate significant efforts, are expensive due to involvement of laboratories and normally may not be executed in the facility the water is treated, especially are not able to be executed online as part of the water treatment process.

SUMMARY

In one embodiment, a method is provided for detecting a concentration of chlorate-ions in an aqueous solution containing different types of chlorine oxidants, comprising the steps of: applying energy to a defined volume of the aqueous solution to trigger a transformation of substantially all chlorine oxidants and/or chlorine therein to chloride and/or chlorate, and detecting the concentration of chlorate-ions contained in the defined volume.

In a further embodiment, the aqueous solution is flowing in a downstream direction and the concentration of chlorate-ions is detected downstream compared to the location the energy is applied. In a further embodiment, the energy is applied by exposing the defined volume to ultra violet radiation for a certain exposure time. In a further embodiment, an intensity of the ultra violet radiation and the exposure time is adjusted such that substantially all chlorine oxidants contained in the defined volume transform to chloride or chlorate. In a further embodiment, the exposure time is adjusted by adjusting the flow rate of the aqueous solution, especially of the defined volume. In a further embodiment, the intensity of the ultra violet radiation is adjusted by adjusting the performance of a ultra violet generating source generating the ultra violet radiation for exposure. In a further embodiment, the expected concentration of chlorate-ions in the aqueous solution is lower than 5 milligram/liter, and comprising following additional steps: detecting a concentration of chlorine and/or chlorite-ions and/or chlorine dioxide before the energy is applied to the defined volume, especially upstream compared to the location the energy is applied for the defined volume, determining the actual chlorate concentration by means of subtracting the detected chlorine concentration and/or the detected chlorite concentration and/or the detected chlorine dioxide concentration from the detected chlorate concentration. In a further embodiment, the transformation is triggered continuously, especially consecutively for a plurality of defined volumes in downstream direction, and the concentration of chlorate-ions is determined by continuous detection of the concentration of chlorate-ions, especially for this plurality of defined volumes. In a further embodiment, the concentration of chlorine and/or chlorite-ions and/or chlorine dioxide is continuously detected before the energy is applied, especially upstream compared to the location the energy is applied, especially for the same plurality of defined volumes. In a further embodiment, the determination of the actual chlorate concentration by means of subtraction is done by using the concentrations detected for the same defined volume or the same plurality of defined volumes. In a further embodiment, a defined volume of the aqueous solution is tracked by using the known flow rate of the aqueous solution and a known reference point for the defined volume.

In another embodiment, a control unit is provided for an apparatus for detection, especially online detection, of a concentration of chlorate-ions in an aqueous solution, comprising program code with control commands, initiating the control unit to execute any of the methods disclosed above.

In another embodiment, an apparatus is provided for detecting, especially online, a concentration of chlorate-ions in an aqueous solution comprising, an energy source applying energy to trigger a transformation in a defined volume of the aqueous solution of substantially all chlorine oxidants and chlorine therein to chloride or chlorate, whereas the applied energy is couplable into the defined volume, and at least one detector to detect a concentration of chlorate-ions, especially positioned downstream to the location the energy is applied.

In a further embodiment, the energy source is an source for emitting ultra violet radiation to irradiate a defined volume of the aqueous solution. In a further embodiment, the detector for detecting a concentration of chlorate-ions is an electrochemical sensor, especially an amperometric sensor or an ion-selective membrane sensor. In a further embodiment, the detector for detecting a concentration of chlorate-ions is an photometric detector. In a further embodiment, the apparatus further comprises at least one additional detector, especially positioned upstream compared to the location the energy is applied to a defined volume, whereas the additional detector is capable to detect chlorine and/or chlorite and/or chlorine dioxide. In a further embodiment, the apparatus comprises a control unit according to claim 12.

BRIEF DESCRIPTION OF THE DRAWINGS

Example embodiments will be explained in more detail below with reference to figures, in which:

FIG. 1 a schematic part of water treatment facility with an apparatus for online-detection of chlorate concentrations above 5 milligram per liter in an aqueous solution, FIG. 2 a flow chart for a schematic visualization of an embodiment of a method for online-detection of chlorate concentrations above 5 milligram per liter in an aqueous solution, FIG. 3 a schematic part of water treatment facility with an apparatus for online-detection of chlorate concentrations below 5 milligram per liter in an aqueous solution, FIG. 4 a flow chart for a schematic visualization of an embodiment of a method for online-detection of chlorate concentrations below 5 milligram per liter in an aqueous solution, FIG. 5 a schematic illustration of photometric measurement system.

DETAILED DESCRIPTION

Figure 3:
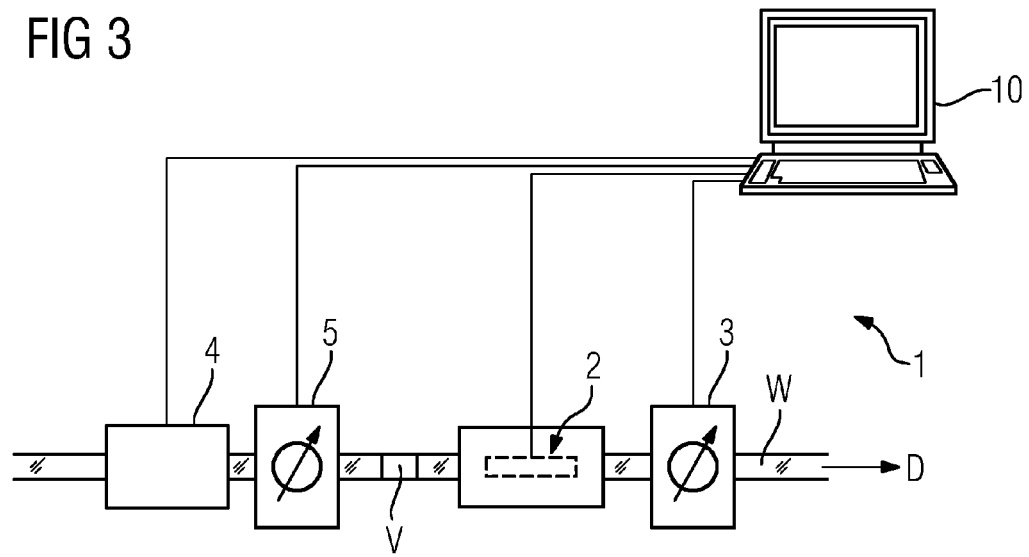

Some embodiments provide a method, an apparatus and a control unit to enable a simple and cheap measurement for a concentration of chlorate ions in an aqueous solution and that is capable for online measurement of such chlorate concentrations.

For example, some embodiments provide a method for detecting a concentration of chlorate-ions in an aqueous solution containing different types of chlorine oxidants, comprising the steps of:

applying energy to a defined volume of the aqueous solution to trigger a transformation of substantially all chlorine oxidants and/or chlorine therein to chloride and/or chlorate, detecting the concentration of chlorate-ions contained in the defined volume, especially with an electrochemical sensor.

This method may provide a simple, cheap and robust technique for measurement of concentrations of chlorate ions that can also be used for online monitoring of chlorate concentrations in aqueous solutions.

An embodiment of this method without further measurements of concentrations of other chlorine species may be advantageous for applications in which the aqueous solution contains a concentration of chlorate before energy is applied to the defined volume that is higher than the concentration of non-chlorate chlorine oxidants (=chlorine oxidant) and/or chlorine in the defined volume.

This is, e.g., the case when concentrations of chlorate in the aqueous solution are expected to be higher than 5 milligram per liter. Especially in swimming pools located in Germany the concentration of chlorate is between 5 and 40 milligram per liter, whereas the concentration of non-chlorate chlorine oxidants, like hypochlorite, and chlorine are in the range of 0.3 milligram per liter. In other countries these values can differ, however the presented method can still be applied, as long as concentration of chlorate-ions is at least 10 times higher than the concentration of chlorine oxidants. In such cases the amount of chlorate created by the transformation, especially photolysis, of the non-chlorate chlorine oxidants and/or chlorine can be neglected, because they lead to a variation of the detected chlorate concentration in a range of 3% or less compared to chlorate contained in the aqueous solution before a transformation is triggered.

Embodiments of the method disclosed herein can be applied for a non-flowing aqueous solution but also for a flowing aqueous solution.

In case of a non-flowing aqueous solution, the detection of the concentration of chlorate-ions is executed—with respect to time—after the energy is applied to trigger the transformation for a defined volume. The detection of a chlorate concentration may be performed within a time range, when the concentration of the chlorine oxidants and/or chlorine has reached a minimum due to the energy applied to the defined volume.

The transformation of substantially all chlorine oxidants and/or chlorine means a transformation reducing non-chlorate chlorine oxidants and/or chlorine such that a chlorate measurement is not significantly disturbed, especially it can mean a 100% transformation of non-chlorate chlorine oxidants and/or chlorine to chlorate within the limits of measurement accuracy, transformation higher than the sum of the amount of the other chlorine oxidants and, if present, the amount of chlorine in the defined volume. Amount means here the amount of substance measured in mol.

The transformation of substantially all chlorine oxidants and/or chlorine contained in the aqueous solution makes it possible to measure chlorate in a technical in a comparably simple manner, especially with an electrochemical sensor.

The energy to trigger the chemical transformation can be applied in any suitable form, which triggers the transformation.

In one embodiment of the method the aqueous solution is flowing in a downstream direction and the concentration of chlorate-ions is detected downstream compared to the location the energy is applied. This may be especially advantageous, if the method is to be used for flowing aqueous solutions, which is regularly the case for water treatment facilities. So the location where the energy is applied to the defined volume is at a different location, e.g. an upstream location compared to the location where the detection of the chlorate concentration takes place.

With respect to the application of energy it may be advantageous to use ultra violet radiation and to irradiate the defined volume for a certain exposure time. This is a technically easy form to apply the energy for the defined volume to trigger the transformation within that defined volume of the aqueous solution. The ultra violet radiation can be generated by every suitable source to generate such radiation. Examples for such UV-sources are low pressure mercury lamps, medium pressure mercury lamps, light emitting diodes able to emit UV radiation with a significant share of power between 100 nm and 400 nm, especially between 200 nm and 400 nm, excimer lamps, and so on. Low pressure mercury lamps may be used for economic reasons. The energy can be applied to the defined volume of the aqueous solution using e.g. a UV transparent quartz.

Furthermore, the application of UV radiation in water treatment is well-known for disinfection purposes, i.e. UV light is used to disinfect the water instead of or additional to chemical substances. So operators of water treatment facilities know how to handle UV sources.

To trigger the transformation in way that substantially all non-chlorate chlorine oxidants do transform it may be preferred that an intensity of the ultra violet radiation and the exposure time is adjusted such that substantially all chlorine oxidants contained in the defined volume transform to chloride and/or chlorate. Goal is to adjust the dose by adjusting the flowrate and lamp parameters. The adjustment can be done by experience or by doing the test runs in the respective facility or modeling.

Especially for flowing aqueous solutions it may be advantageous to adjust the exposure time by adjusting the flow rate of the aqueous solution, especially of the defined volume. Using this embodiment the UV source can be operated constantly, especially continuously. So lifetime of the UV source can be maximized. It may therefore be preferred that the flow rate is adjusted upstream to the location the energy is applied to the defined volume.

The intensity of the ultra violet radiation can preferably be adjusted by adjusting the electric performance of the UV source.

However, also a device separate of the UV source can be used to adjust the intensity of the UV radiation interacting with the defined volume, like UV absorbers with different absorption properties. This makes it possible to operate the UV source under relatively constant conditions. So lifetime of the UV source is increased.

In a further embodiment the method is performed for an aqueous solution with a concentration of chlorate-ions in the aqueous solution lower than 5 milligram/liter before applying energy to the defined volume, and comprises following additional steps:

detecting a concentration of chlorine and/or chlorite-ions and/or chlorine dioxide before the energy is applied for the defined volume, especially upstream compared to the location the energy is applied for the defined volume, determining the actual chlorate concentration by means of subtracting the detected chlorine concentration and/or the detected chlorite concentration and/or the detected chlorine dioxide concentration from the detected chlorate concentration.

The actual chlorate concentration is the concentration of chlorate in the defined volume before energy is applied to trigger the transformation of the non-chlorate-chlorine oxidants, respectively chlorine to chlorate and/or chloride.

Such embodiment may be advantageously used for drinking water application, which usually has a concentration of chlorate of less than 5 milligram per liter before the energy is applied to the defined volume. Therefore the method can also be used for concentrations of chlorate below 5 milligram per liter in an aqueous solution.

If the detected signals for the chlorate, chlorite, chlorine respectively chlorine dioxide is transmitted to a control unit, the subtraction can be done automatically. So the actual chlorate concentration can be determined fast and exact, especially in real-time, which allows online monitoring of the actual chlorate concentration.

In one embodiment of the method the aqueous solution is flowing in a downstream direction and the concentration of chlorate-ions is detected downstream compared to the location the energy is applied. So the location of detection of chlorate and the location the energy is applied to the defined volume are different. Such procedure may be especially advantageous in case of continuous determination of the actual chlorate concentrations. E.g. therefore the quality of drinking water with respect to the content of chlorate in the water can be monitored all-over.

In some embodiments it may be preferred to detect the concentration of chlorine and/or chlorite-ions and/or chlorine dioxide is continuously before the energy is applied, especially upstream compared to the location the energy is applied, especially for the same plurality of defined volumes. Such procedure may be especially advantageous in case of continuous determination of the actual chlorate concentrations. E.g. therefore the quality of drinking water with respect to the content of chlorine and/or chlorite-ions and/or chlorine dioxide in the water can be monitored all-over. This allows determining the actual chlorate concentration with help of the above mentioned subtraction step all-over.

Furthermore it may be advantageous that the determination of the actual chlorate concentration by means of subtraction is done by using the concentrations detected for the same defined volume or the same plurality of defined volumes. This means, the concentration of chlorine species and/or chlorite-ions and/or chlorine dioxide is detected for certain specific defined volume aqueous solution, especially upstream compared to the location the energy is applied to the same defined volume. Flowing in downstream direction this defined volume for which the concentrations of chlorine and/or chlorite-ions and/or chlorine dioxide have been detected is then transformed, photolized e.g. by the UV radiation, which triggers the transformation of chlorine and/or chlorite-ions and/or chlorine dioxide to chloride and chlorate. Then for this same defined volume the concentration of chlorate is detected downstream compared to the location the energy was applied. This means, all measured data refer to the same defined volume. Determining the actual concentration of chlorate this way the accuracy of the measurement is increased and very exact values of chlorate concentrations can be determined.

If the defined volume does flow continuously from the location where the concentration of chlorine and/or chlorite-ions and/or chlorine dioxide is detected to the location, where the chlorate concentration is detected, the volume can be tracked easily by utilizing the known flow rate of the defined volume. In such a case, the signals for chlorine and/or chlorite-ions and/or chlorine dioxide and the signal of chlorate for the same defined volume correlate with a time shift corresponding to the time needed by the defined volume to travel from the location of the detection of concentrations of chlorine and/or chlorite-ions and/or chlorine dioxide to the location of the detection of concentrations of chlorate. This can be used to realize such method. Signals for concentrations detected at different times are subtracted in the subtraction step. Therefore it may be advantageous to assign a time stamp to the detected signals corresponding to the respective concentration. This may be advantageously done by the detector to avoid failures by signal runtime errors.

Some embodiments provide a control unit for an apparatus for online detection of a concentration of chlorate-ions in an aqueous solution, comprising program code with control commands, initiating the control unit to execute the method according to one of the claims 1 to 11.

Further, some embodiments provide an apparatus for detecting, especially online, a concentration of chlorate-ions in an aqueous solution comprising, an energy source for applying energy to a defined volume of the aqueous solution to trigger a transformation of substantially all chlorine oxidants and chlorine therein to chloride and/or chlorate, whereas the energy is couplable into the defined volume, and at least one detector to detect a concentration of chlorate-ions, especially positioned downstream to the location the energy is applied.

Such an apparatus allows to measure chlorate concentration easily and the makes it possible to do online-monitoring of chlorate concentration in a water treatment facility. Such can be used to determine chlorate concentrations in case the chlorate concentration in the aqueous solution is high compared to the concentration of other chlorine species, i.e. at least 10 times higher.

Detector is any apparatus suitable to detect a chlorate concentration.

In one embodiment the energy source is a source for emitting ultra violet radiation to irradiate a defined volume of the aqueous solution. This is a technical simple and robust solution without high maintenance efforts, see respective passage above.

In case of the use of UV radiation as energy the radiation can be coupled into the defined volume of the aqueous solution e.g. via a UV transparent quartz of the water treatment facility to trigger the above mentioned transformation.

In one embodiment of the apparatus the detector for detecting a concentration of chlorate-ions is an electrochemical sensor, especially an amperometric sensor or an ion-selective membrane sensor. Such detector can be positioned at the place where the energy is applied to the defined volume. In an alternative embodiment such detector can be positioned downstream compared to the location the energy is applied. This may be advantageous in case of a flow rate of the defined volume in downstream direction which is substantially unequal to zero, i.e. the defined volume of the aqueous solution is flowing. The second embodiment may be the preferred embodiment, if the chlorate concentration is to be detected online in a water treatment facility.

In another embodiment of the apparatus the detector for detecting a concentration of chlorate-ions is a photometric detector. This may be especially advantageous when the flow rate of the defined volume is substantially zero, i.e. the aqueous solution is not flowing. If calibrated regularly, this measurement can be done in water treatment facility, i.e. on the site. No special and distanced water laboratory is needed.

For such a measurement, the defined volume of the aqueous solution is irradiated for a certain time and with a certain intensity to transform all chlorine oxidants and/or chlorine to chlorate. After the transformation has taken place, a first substance can be added to the aqueous solution to transform the present chlorate ion concentration into a second substance detectable with a photometer, e.g. the second substance can be haloquinone, which leads to a yellow color of the aqueous solution that absorbs radiation emitted by the photometer. By measuring the absorption of such a colored aqueous solution—whereas the "density" of the color reflects to concentration of chlorate ions on the solution—the concentration of the solution can be determined quite easily.

Several protocols are known to transform chlorite ions into an absorptive substance. Examples for such protocols have been published 2009 by Hosseini et al., "Spectrophotometric determination of chlorate ions in Drinking water", Desalination 245, pages 298-305, or by Trautwein and Guyon 1968, "Spectrophotometric Determination of Chlorate Ion", Anal. Chim. Acta, 41, pages 275-282.

Using a photometer is as well an easy and inexpensive way to sample chlorate ions on site and can be used for separated samples out of a flowing or non-flowing aqueous solution to be investigated.

Electrochemical sensors, like amperometric sensor or an ion-selective membrane sensor, are common, comparably cheap, reliable and easy to handle. They allow therefore an online measurement of chlorate concentrations in a defined volume, if the above mentioned transformation was triggered.

To determine chlorate concentrations which are high compared to the concentration of residual chlorine species, i.e. at least 10 times higher, it may be advantageous if the apparatus comprises at least one additional detector, especially positioned upstream compared to the location the energy is applied to a defined volume, whereas the additional detector is capable to detect chlorine and/or chlorite and/or chlorine dioxide. With this detector the signals can be provided to determine the chlorate concentration according to the "subtraction" method, see above.

In a special embodiment apparatus comprises a control unit according to claim 12. The control unit operatively interacts with at least the detector detecting chlorate concentration. Additionally, the control unit can operatively interact with the detector detecting concentrations of chlorine and/or chlorite and/or chlorine dioxide and/or the energy source to provide energy for the transformation in the defined volume. The control unit may comprise program code to process the signals received from the detectors as discussed herein. This may be especially advantageous in case of an automatic and continuous monitoring of the chlorate concentration in a water treatment facility.

FIG. 1 shows a part of water treatment facility in which water is processed which normally has a chlorate concentration of 5 milligram per liter or more. This is e.g. the case in water used in private or public swimming pools in Germany using chlorine species for disinfection.

Dependant on what chlorine species are used to disinfect the water different chlorine oxidants can appear in the water. In case of disinfection using chlorine, there is chlorine, chloride, hypochlorite, chlorite and chlorate in the water. In case of disinfection using chorine dioxide there is chlorine dioxide, chlorite and chlorate in the water.

FIG. 1 shows an apparatus 1 capable for online-detection and online monitoring for chlorate concentration in such water W.

In this example an online-detection respectively online monitoring of chlorate concentration may be advantageous, because the water W is continuously treated in terms of disinfection and therefore the concentration of chlorate should be monitored continuously. Due to the continuous treatment process, the water W is continuously flowing in a downstream direction D.

The apparatus 1 comprises an energy source 2 to provide energy to a defined volume V of the water W. In this example, the energy source 2 is a lamp 2 able to emit ultra violet radiation. The water is guided around the lamp to ensure that the maximum of the emitted UV light will interact with the aqueous solution. This UV radiation, if interacting with the substances a defined volume V, can trigger a transformation of chlorine, hypochlorite, chlorite or chlorine dioxide to chloride and/or chlorate in that defined volume V. As UV source UV lamps can be used available on the market.

Furthermore, the apparatus 1 comprises a detector 3 to continuously detect a concentration of chlorate in the water. In the example, the detector 3 is positioned downstream compared to the location the radiation is interacting with the defined volume V. The distance between the location of applying the radiation to the defined volume V and the position of the detector 3 is adjusted in way that the transformation triggered by the radiation has transformed substantially all chlorine, hypochlorite, chlorite and chlorine dioxide, as far as contained in the volume, to chloride and chlorate.

In this case, an electrochemical sensor can be used as detector 3 to detect the concentration of chlorate in the water W at the location of detection.

Additional, a flow meter can be used to determine the flow rate of the water. The flow meter in this example is also capable to adjust the flow rate. However, adjustment of the flow rate and measurement of the flow rate can also be realized by using two different devices for these tasks.

The flow meter in this example is positioned upstream to the location the UV radiation is applied to water W. This allows adjusting the radiation parameters respectively the parameters of the lamp to the flow rate. But also adjusting the flow rate before the water reaches the location it is irradiated by UV radiation.

Adjusting the flow rate and the parameters of the UV source enable the operator the adjust a dose sufficient to trigger the transformation in a defined volume V.

In this example, the irradiated area by the UV lamp is constant. However, in case of different flow rates, the exposure time for a defined volume is different flowing in downstream direction D. This however is dependant on the fact, if the flow is laminar or turbulent. To ensure a sufficient dose the intensity of UV radiation and/or the flow rate of the water to be irradiated can be adjusted. Generally, for a lower exposure time, i.e. higher flow rate, a higher intensity is needed as for a high exposure time, i.e. lower flow rate, of the defined volume to trigger the transformation.

The flow meter 4, the UV source 2 and the detector 3 are operatively connected to a control unit 10. The control unit 10 receives signals from all these flow meter 4, the UV source 2 and the detector 3. The control unit can also send signals, especially control signals, to these devices, e.g. to adjust the power of the UV source or the flow rate.

The control unit 10 comprises therefore program code incorporating control commands to realize such signal communication and/or control of the connected devices.

E.g., in the case of German swimming pools, around 0.3 milligram per liter free chlorine are applied as hypochlorite or chlorine gas. Therefore the increase in chlorate concentration is around 0.15 milligram per liter expected for 0.3 milligram per liter chlorine with a detection limit of 5 mg/L chlorate. Assuming that a regular concentration of chlorate in swimming pool water is between 5 to 40 milligram per liter, the deviation of the actual chlorate concentration after UV radiation caused by the triggered transformation would be around 3 percent or less. So this effect can be neglected. Otherwise it can be taken into account with the help of a calibration factor. The chlorate sensor used for such application can be an open cell amperometric or membrane ion-selective sensor with a sensitive response.

Within water streams of 600 milliliter per minute, an electric power of 20 to 100 Watt of the UV lamp with a regular radiation area is expected to achieve the needed reduction of chlorine and chlorine oxidants of 0.3 milligram per liter free chlorine to the detection limit for the electrochemical sensor.

It may be assured by test runs that the applied energy, e.g. the provided dose of UV radiation, is sufficient for the aspired transformation.

FIG. 2 shows a flow chart visualizing a possible method that can be run on the apparatus shown in FIG. 1.

The flow chart is based on the assumption that there is already water flowing through a water treatment facility for which chlorate concentration should be detected using an apparatus according to FIG. 1.

In a first step 100 the flow rate is measured using the flow meter. This information is provided to the control unit.

Based on this information the control unit sends a signal to the flow meter to adjust the flow rate and/or the parameters of the UV source, to assure that the transformation of the chlorine oxidants and/or Chlorine in the water will transform in the defined volume to chlorate and chloride after this volume has been exposed to the UV radiation for the exposure time. This is done in a step 101.

In a step 102 the defined volume of water will be exposed to the UV radiation, which triggers the above transformation.

After substantially all of the chlorine oxidants and/or Chlorine transformed to chlorate and chloride the concentration of chlorate is measured in a step 103 with an electrochemical sensor. This signal for chlorate concentration is transmitted to the control unit. In the control unit a calibration factor can be applied to the signal to improve accuracy of the measurement. This is however optional.

This procedure can be executed as long as the water shall be check for chlorate concentration. If the method shall be stopped, is checked in step 104. If not, the method repeats until it is stopped.

FIG. 3 shows an apparatus 1 according to FIG. 1 with an additional detector 5. Same reference signs have the same meaning as in FIG. 1.

Such a layout can be used in water treatment application dealing with drinking water. Normally, such water has a chlorate concentration of less than 5 milligram per liter, especially less than 1 milligram per liter.

The additional detector 5 can stand for several detectors capable to measure the concentration of chlorine, hypochlorite, and chlorite, respectively chlorine dioxide and chlorite, dependant on the fact, if chlorine or chlorine dioxide is added as disinfectant to the water. The signals measured for the concentration of these chlorine species are transmitted to the control unit 10. The detector 5 is positioned upstream to the UV source 2 and the detector 3.

The position of the defined volume V may be tracked by knowing the flow rate and distance between the additional detectors, if more than detector is used to detect the concentrations for the above named chlorine species. This allows assigning specific concentration signals of the above mentioned chlorine species to a specific defined volume of water.

In specific embodiment, the control unit 10 is capable to adjust the power of the UV radiation and the UV exposure time for the defined volume in dependence of the detected concentration signals of chlorine, hypochlorite, and chlorite, respectively chlorine dioxide and chlorite. This may be used in case of high concentration fluctuation, which however are normally not the case.

Afterwards, the defined volume V for which the above signals are detected flows downstream to the location the energy is applied to that defined volume. After the UV radiation has been applied using the UV source 2, the defined volume V propagates in downstream direction to the location the concentration of chlorate is detected with detector 3. The signal of the chlorate concentration is transmitted to the control unit 10.

The concentration detected with detector 3 is however not the "normal" chlorate concentration in the treated water. So the actual chlorate concentration needs to be calculated by a subtraction of different detected concentrations. This is done automatically in the control unit 10. Further details will be disclosed in context with FIG. 4. The result for the actual chlorate concentration is then e.g. displayed at a monitor.

Figure 4:
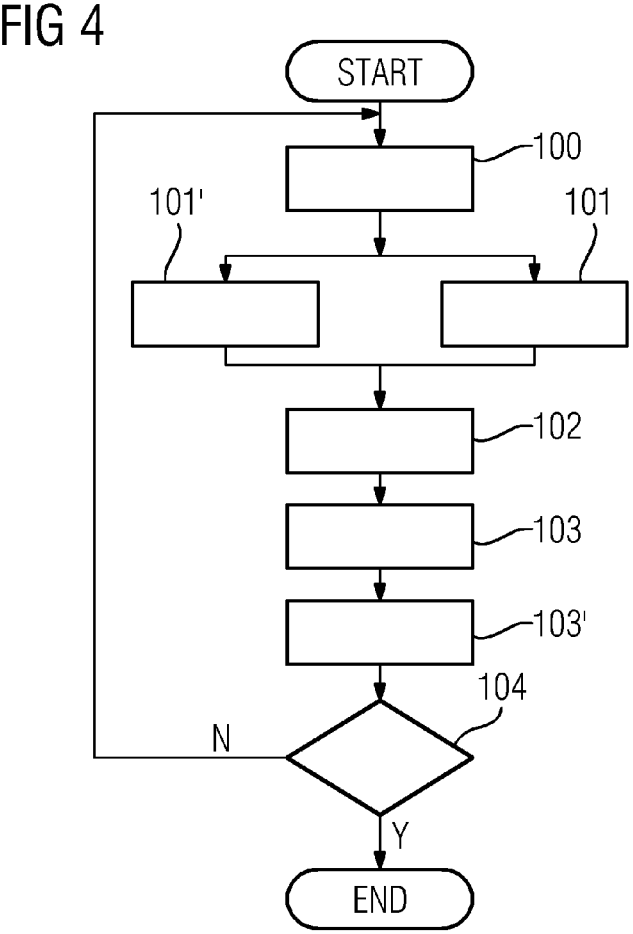

FIG. 4 shows an example for a method using an apparatus according to FIG. 3.

In a first step 100 the flow rate of the water is detected at a position upstream of the location the energy is provided to a defined volume of the water.

The signal representing the flow rate is transmitted to the control unit, which can use it for further processing.

In a step 101 the flow rate and/or the parameters of the UV source are adjusted, e.g. in dependence of an actual or to be adjusted flow rate. In parallel the concentration of chlorine, hypochlorite and chlorite, respectively the concentration of chlorine dioxide and chlorite is detected in a step 101' using the detector(s) 5 in FIG. 3. The signals corresponding to these concentrations are transmitted to the control unit.

Subsequently, the volume for which the concentrations have been detected is exposed to UV radiation for a certain exposure time, leading to transformation the chlorine oxidants to chloride and/or chlorate. This is done in the step 102.

Downstream compared to the location of exposure of the volume to UV radiation, the chlorate concentration is detected with a detector 3, like an electrochemical sensor. The signal corresponding to the detected chlorate concentration is transmitted to the control unit.

In the control unit the detected signals are processed in step 103'. The processing of the data can happen in different ways.

E.g, a first possibility is to subtract the concentrations detected for the identical volume element, i.e. the runtime of the volume from the additional detector(s) 5 to the detector 3 according FIG. 3 needs to be taken into account and is to be considered for the determination of the actual chlorate concentration. This runtime can be determined by the flow rate and the distance between the detectors. The subtraction is then performed for detected concentrations which have the determined runtime difference. So the subtraction is made for signals that are assigned to the same defined volume of the water. Such a processing increases accuracy of the determined actual chlorate concentration.

Another possibility is to subtract the concentration without considering the runtime of a defined volume, i.e. the concentrations of chlorate and the concentrations of chlorine, hypochlorite, chlorite, respectively chlorine dioxide and chlorite. The detections at detector 3 and detector 5 are running continuously and the detected concentrations of detector 5 are subtracted from the detected concentrations of detector 3. In this case, signals are subtracted which are not assigned to the same defined volume but are assigned to different defined volumes.

In case of a disinfection based on the adding of chlorine, the following subtraction can be made:

$$M(\text{chlorate(after UV)})*\text{calibration factor}-(M(\text{chlorine})+M(\text{chlorite}))=M(\text{chlorate(before UV)})$$

"M" means here molar concentration of the respective substance in brackets. The concentration of "chlorate (before UV)" is also named "actual chlorate concentration", see above.

The calibration factor can be defined by test runs or can be found in literature. The calibration factor is also dependant, on the substance added to the aqueous solution for disinfection, chlorine or chlorine dioxide.

The presented methods and other embodiments of the method disclosed herein can run continuously and for plurality of defined volumes in parallel which may be advantageous for allover real-time monitoring of water quality.

In a step 104 it is checked, if the method shall be stopped. As long as no decision is taken to stop the method, the method will be running.

Figure 5:
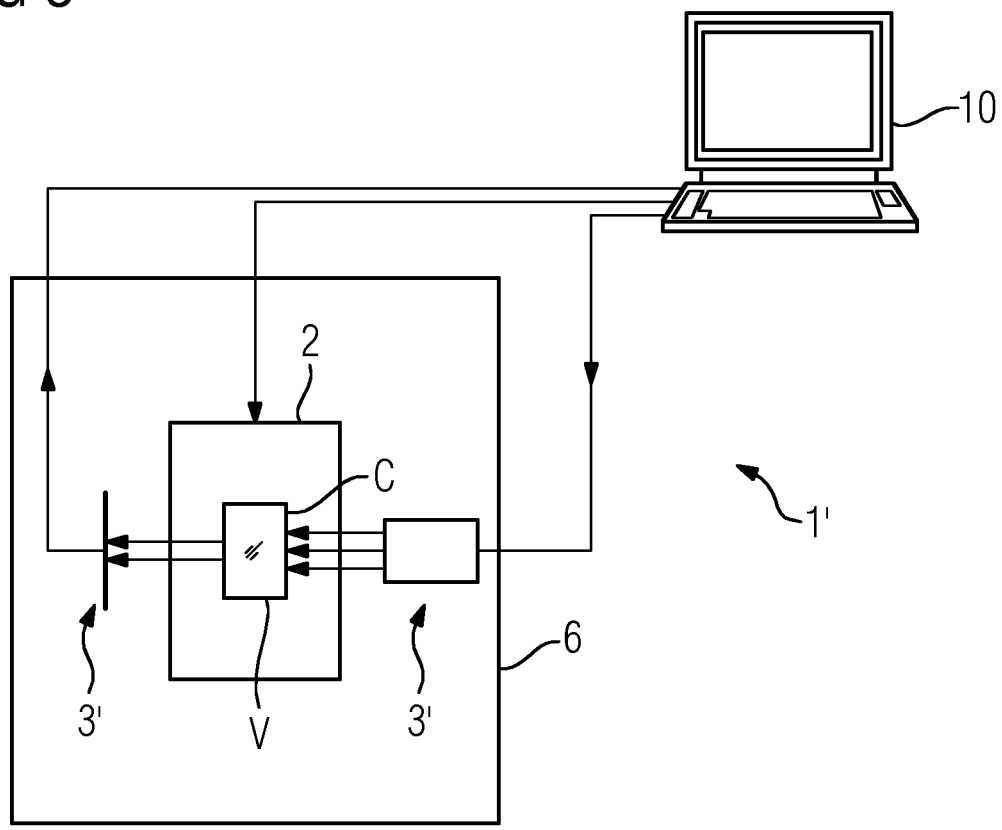

FIG. 5 shows an assembly 1' using a detector realized as photometer 3' to detect chlorate ions in a defined volume V of an aqueous solution. In this embodiment, a defined volume V of the aqueous solution is taken from a flowing or a non-flowing aqueous solution. The defined volume is V contained in a UV transparent case C, e.g. a UV transparent vial.

Dependant on what concentrations are expected, a first measurement can take place by using the photometer 3' to detect the concentration of chlorine and/or chlorine oxidants in the defined volume V. This is e.g. the case, if the concentration of the chlorine and/or the chlorine oxidants is similar or higher compared to the concentration of chlorate ions in the defined volume V before irradiation of the defined volume with UV light.

In case the concentration of chlorate ions is significantly higher than the concentration of chlorine and/or chlorine oxidants no such first measurement before irradiation of the defined volume V needs necessarily to be made.

Then the defined volume in the vial is exposed to UV radiation to transform the chlorine and/or chlorine oxidants to chlorate. This is done using an UV source 2, esp. low pressure or medium pressure UV lamp. To protect the environment from the UV radiation, the UV exposure is taking place in a radiation chamber 6.

After the transformation the concentration of chlorate ions is measured by an absorption measurement using the photometer 3'. The photometer 3' may be connected to a control unit 10, controlling the UV source and the photometer. So the signals measurement can be initiated and received signals can be processed via the control unit 10.

With the photometer 3' normally no online measurement can be provided for a water treatment facility, however an on site analysis can be performed, which is—compared to the current status of chlorate analysis—already a big step forward. In addition customers are used to do photometric on site measurements in other context. Therefore customers will be open for such kind of measurements.

What is claimed is:

1. A method for determining an actual concentration of chlorate ions in an aqueous solution, comprising:
   detecting a total concentration of chlorine, chlorite, and chlorine dioxide in a defined volume of the aqueous solution;
   applying energy to the defined volume of the aqueous solution to transform substantially all chlorine species therein to chloride and chlorate;
   detecting a concentration of chlorate ions in the defined volume after the energy is applied; and
   subtracting the total concentration of chlorine, chlorite, and chlorine dioxide from the detected concentration of chlorate ions contained in the defined volume after the energy is applied to determine the actual concentration of chlorate ions in the aqueous solution.

2. The method of claim 1, wherein the aqueous solution is flowing in a water treatment facility.

3. The method of claim 2, wherein the concentration of chlorate ions in the defined volume is detected downstream of an energy source.

4. The method of claim 3, wherein the energy is applied by exposing the defined volume to ultraviolet radiation for an exposure time.

5. The method of claim 4, further comprising adjusting an intensity of the ultraviolet radiation to promote the transformation to chloride and chlorate.

6. The method of claim 4, further comprising adjusting the exposure time to promote the transformation to chloride and chlorate.

7. The method of claim 6, wherein the exposure time is adjusted by adjusting a flow rate of the aqueous solution.

8. The method of claim 7, wherein the flow rate is adjusted prior to applying energy to the defined volume.

9. The method of claim 5, wherein the intensity of the ultraviolet radiation is adjusted by adjusting a power or wavelength parameter of a source of the ultraviolet radiation.

10. The method of claim 1, wherein a target concentration of chlorate ions in the aqueous solution is lower than 5 mg/L.

11. The method of claim 1, wherein the concentration of chlorate ions in the aqueous solution is measured online as part of a water treatment process.

12. The method of claim 1, wherein the energy is applied consecutively to a plurality of defined volumes.

13. The method of claim 12, wherein the concentration of chlorate ions in the plurality of defined volumes is detected after the energy is applied.

14. The method of claim 13, wherein the actual concentration of chlorate ions in the aqueous solution is determined based on the detected concentration of chlorate ions in the plurality of defined volumes.

15. The method of claim 14, wherein the actual concentration of chlorate ions in the aqueous solution is determined continuously.

16. The method of claim 1, wherein the total concentration of chlorine, chlorite, and chlorine dioxide is continuously detected before the energy is applied.

17. The method of claim 13, wherein the actual chlorate concentration is based on the total concentration of chlorine, chlorite, and chlorine dioxide and the detected chlorate concentration for the same defined volume or the same plurality of defined volumes.

18. The method of claim 17, wherein a location of a defined volume of the aqueous solution is tracked based on a flow rate of the aqueous solution or a known reference point for the defined volume.

19. The method of claim 9, wherein the wavelength parameter is between about 100 nm and about 400 nm, and wherein the power is between about 20 W and about 100 W.

20. The method of claim 11, wherein the concentration of chlorate ions in the aqueous solution is measured with an amperometric sensor.

* * * * *